US011623053B2

(12) United States Patent
Yilmaz et al.

(10) Patent No.: US 11,623,053 B2
(45) Date of Patent: Apr. 11, 2023

(54) COMPONENT FOR AN AEROSOL-GENERATING APPARATUS

(71) Applicant: NICOVENTURES TRADING LIMITED, London (GB)

(72) Inventors: Ugurhan Yilmaz, London (GB); Mark Potter, London (GB)

(73) Assignee: Nicoventures Trading Limited, London (GB)

( * ) Notice: Subject to any disclaimer, the term of this patent is extended or adjusted under 35 U.S.C. 154(b) by 332 days.

(21) Appl. No.: 15/733,181

(22) PCT Filed: Dec. 5, 2018

(86) PCT No.: PCT/EP2018/083665
§ 371 (c)(1),
(2) Date: Jun. 4, 2020

(87) PCT Pub. No.: WO2019/110669
PCT Pub. Date: Jun. 13, 2019

(65) Prior Publication Data
US 2021/0084982 A1 Mar. 25, 2021

(30) Foreign Application Priority Data
Dec. 6, 2017 (GB) .................................. 1720338

(51) Int. Cl.
*A24F 40/44* (2020.01)
*A24F 40/46* (2020.01)
(Continued)

(52) U.S. Cl.
CPC ............ *A61M 15/06* (2013.01); *A24F 40/30* (2020.01); *A24F 40/42* (2020.01); *A24F 40/44* (2020.01);
(Continued)

(58) Field of Classification Search
CPC .......... A24F 40/10; A24F 40/20; A24F 40/30; A24F 40/42; A24F 40/44; A24F 40/46;
(Continued)

(56) References Cited

U.S. PATENT DOCUMENTS 2,153,623 A 4/1939 Jacobson
2,956,568 A 10/1960 Magnus et al.
(Continued)

FOREIGN PATENT DOCUMENTS

AR 089648 A1 9/2014
AR 091949 A1 3/2015
(Continued)

OTHER PUBLICATIONS

Application and File History for U.S. Appl. No. 15/733,181, filed Jun. 4, 2020, inventor Yilmaz.
(Continued)

*Primary Examiner* — Hae Moon Hyeon
*Assistant Examiner* — Thang H Nguyen
(74) *Attorney, Agent, or Firm* — Patterson Thuente, P.A.

(57) ABSTRACT

A component for an aerosol-generating apparatus includes a liquid container for containing liquid, a wick arranged to draw liquid from the liquid container in use; and a heater arranged to volatilize liquid drawn from the liquid container by the wick in use to generate an aerosol in use. The heater defines a channel for receiving a material element for modifying a property of the aerosol generated in use. The component is arranged such that, in use, the material element received in the channel in use modifies a property of the aerosol generated in use thereby to generate a modified aerosol for inhalation by a user.

24 Claims, 2 Drawing Sheets

(51) Int. Cl.
    *A24F 40/48*     (2020.01)
    *A61M 15/06*     (2006.01)
    *A24F 40/30*     (2020.01)
    *A24F 40/42*     (2020.01)
    *A24F 40/10*     (2020.01)
    *A24F 40/20*     (2020.01)

(52) U.S. Cl.
    CPC .............. *A24F 40/46* (2020.01); *A24F 40/48* (2020.01); *A24F 40/10* (2020.01); *A24F 40/20* (2020.01)

(58) Field of Classification Search
    CPC . A24F 40/48; A61M 11/042; A61M 15/0003; A61M 15/06; A61M 2205/3653; A61M 2205/8206
    See application file for complete search history.

(56) References Cited

U.S. PATENT DOCUMENTS

| | | |
|---|---|---|
| 3,339,557 A | 9/1967 | Karalus |
| 3,468,316 A | 9/1969 | Baum et al. |
| 4,038,994 A | 8/1977 | Aikman |
| 4,227,540 A | 10/1980 | Edison |
| 4,338,931 A | 7/1982 | Cavazza |
| 4,478,228 A | 10/1984 | Chister |
| 4,484,590 A | 11/1984 | Singh |
| 4,559,955 A | 12/1985 | Brockway et al. |
| 4,637,407 A | 1/1987 | Bonanno et al. |
| 4,677,995 A | 7/1987 | Kallianos et al. |
| 4,848,375 A | 7/1989 | Patron et al. |
| 4,945,931 A | 8/1990 | Gori |
| 4,991,605 A | 2/1991 | Keritsis |
| 5,060,671 A | 10/1991 | Counts et al. |
| 5,095,921 A | 3/1992 | Losee et al. |
| 5,105,831 A | 4/1992 | Banerjee et al. |
| 5,322,075 A | 6/1994 | Deevi et al. |
| 5,408,574 A | 4/1995 | Deevi et al. |
| 5,468,936 A | 11/1995 | Deevi et al. |
| 5,573,692 A | 11/1996 | Das et al. |
| 5,819,756 A | 10/1998 | Mielordt |
| 5,865,186 A | 2/1999 | Volsey, II |
| 5,878,752 A | 3/1999 | Adams et al. |
| 6,336,896 B1 | 1/2002 | Hsu et al. |
| 6,382,465 B1 | 5/2002 | Greiner-Perth |
| 6,606,992 B1 | 8/2003 | Schuler et al. |
| 6,705,313 B2 | 3/2004 | Niccolai |
| 6,708,846 B1 | 3/2004 | Fuchs et al. |
| 7,374,063 B2 | 5/2008 | Reid |
| 7,658,197 B1 | 2/2010 | Villagomez |
| 8,377,009 B2 | 2/2013 | Sullivan et al. |
| 8,997,753 B2 | 4/2015 | Li et al. |
| 8,997,754 B2 | 4/2015 | Tucker et al. |
| 9,004,073 B2 | 4/2015 | Tucker et al. |
| 9,247,773 B2 | 2/2016 | Memari et al. |
| 9,282,772 B2 | 3/2016 | Tucker et al. |
| 9,693,587 B2 | 7/2017 | Plojoux et al. |
| 10,010,687 B2 | 7/2018 | Von Schuckmann |
| 10,426,199 B2 | 10/2019 | Turner et al. |
| 10,470,491 B2 | 11/2019 | Sutton et al. |
| 10,492,526 B2 | 12/2019 | Sampson et al. |
| 10,758,686 B2 * | 9/2020 | Reevell .................. A24F 40/30 |
| 11,033,055 B2 * | 6/2021 | Fraser .................... A24F 40/42 |
| 2002/0079377 A1 | 6/2002 | Nichols |
| 2003/0183616 A1 | 10/2003 | Goto |
| 2004/0237974 A1 | 12/2004 | Min |
| 2005/0000518 A1 | 1/2005 | Dunkley et al. |
| 2005/0016533 A1 | 1/2005 | Schuler et al. |
| 2005/0022813 A1 | 2/2005 | Alston |
| 2005/0048003 A1 | 3/2005 | Ohki et al. |
| 2005/0056280 A1 | 3/2005 | Alston et al. |
| 2005/0081852 A1 | 4/2005 | Rangachari |
| 2005/0126568 A1 | 6/2005 | Davies et al. |
| 2005/0150492 A1 | 7/2005 | Dunkley et al. |
| 2006/0272659 A1 | 12/2006 | Kobal et al. |
| 2007/0012327 A1 | 1/2007 | Karles et al. |
| 2008/0053465 A1 | 3/2008 | Tarora et al. |
| 2008/0092912 A1 | 4/2008 | Robinson et al. |
| 2010/0200006 A1 | 8/2010 | Robinson et al. |
| 2011/0126848 A1 | 6/2011 | Zuber et al. |
| 2013/0037041 A1 | 2/2013 | Worm et al. |
| 2013/0037042 A1 | 2/2013 | Hearn et al. |
| 2013/0042865 A1 | 2/2013 | Monsees et al. |
| 2013/0068081 A1 | 3/2013 | Kronberg et al. |
| 2013/0192615 A1 | 8/2013 | Tucker et al. |
| 2013/0192616 A1 | 8/2013 | Tucker et al. |
| 2013/0192619 A1 | 8/2013 | Tucker et al. |
| 2013/0192620 A1 | 8/2013 | Tucker et al. |
| 2013/0192621 A1 | 8/2013 | Li et al. |
| 2013/0192622 A1 | 8/2013 | Tucker et al. |
| 2013/0192623 A1 | 8/2013 | Tucker et al. |
| 2013/0298905 A1 | 11/2013 | Levin et al. |
| 2013/0312742 A1 | 11/2013 | Monsees et al. |
| 2013/0333709 A1 | 12/2013 | Shimizu |
| 2014/0060556 A1 | 3/2014 | Liu |
| 2014/0202479 A1 | 7/2014 | Nicholls et al. |
| 2014/0209105 A1 | 7/2014 | Sears et al. |
| 2014/0366898 A1 | 12/2014 | Monsees et al. |
| 2015/0027469 A1 | 1/2015 | Tucker et al. |
| 2015/0027477 A1 | 1/2015 | Yoshino et al. |
| 2015/0245654 A1 | 9/2015 | Memari et al. |
| 2015/0245655 A1 | 9/2015 | Memari et al. |
| 2015/0245656 A1 | 9/2015 | Memari et al. |
| 2015/0245657 A1 | 9/2015 | Memari et al. |
| 2015/0245662 A1 | 9/2015 | Memari et al. |
| 2015/0245663 A1 | 9/2015 | Memari et al. |
| 2015/0245664 A1 | 9/2015 | Memari et al. |
| 2015/0245665 A1 | 9/2015 | Memari et al. |
| 2015/0245666 A1 | 9/2015 | Memari et al. |
| 2015/0245667 A1 | 9/2015 | Memari et al. |
| 2015/0245668 A1 | 9/2015 | Memari et al. |
| 2015/0272219 A1 | 10/2015 | Hatrick et al. |
| 2015/0359266 A1 | 12/2015 | Memari et al. |
| 2015/0374035 A1 | 12/2015 | Sanchez et al. |
| 2016/0007648 A1 | 1/2016 | Sutton et al. |
| 2016/0007649 A1 | 1/2016 | Sampson et al. |
| 2016/0206005 A1 | 7/2016 | Yamada et al. |
| 2016/0295922 A1 | 10/2016 | John et al. |
| 2016/0324216 A1 | 11/2016 | Li et al. |
| 2016/0331034 A1 | 11/2016 | Cameron |
| 2016/0345632 A1 | 12/2016 | Lipowicz |
| 2017/0055575 A1 | 3/2017 | Wilke et al. |
| 2017/0055580 A1 | 3/2017 | Blandino et al. |
| 2017/0055581 A1 | 3/2017 | Wilke et al. |
| 2017/0055582 A1 | 3/2017 | Blandino et al. |
| 2017/0055583 A1 | 3/2017 | Blandino et al. |
| 2017/0055584 A1 | 3/2017 | Blandino et al. |
| 2017/0071251 A1 * | 3/2017 | Goch .................... A24F 40/485 |
| 2017/0086501 A1 | 3/2017 | Buehler et al. |
| 2017/0238611 A1 | 8/2017 | Buchberger |
| 2017/0245553 A1 | 8/2017 | Reevell |
| 2017/0251723 A1 | 9/2017 | Kobal et al. |
| 2017/0319799 A1 | 11/2017 | Yamada et al. |
| 2017/0347706 A1 | 12/2017 | Aoun et al. |
| 2018/0007966 A1 | 1/2018 | Li et al. |
| 2018/0027882 A1 | 2/2018 | Hepworth et al. |
| 2018/0035719 A1 * | 2/2018 | Turner .................. A61M 15/06 |
| 2018/0221605 A1 * | 8/2018 | Marks .................... A24F 40/46 |
| 2018/0279678 A1 * | 10/2018 | Hepworth ............ A61M 11/042 |
| 2018/0360122 A1 | 12/2018 | Aoun et al. |
| 2019/0098930 A1 | 4/2019 | Fallon et al. |
| 2019/0124978 A1 | 5/2019 | Liu |
| 2019/0125988 A1 | 5/2019 | Trzecieski |
| 2019/0230990 A1 | 8/2019 | Hepworth |
| 2019/0254343 A1 | 8/2019 | Hepworth et al. |
| 2019/0254344 A1 | 8/2019 | Hepworth et al. |
| 2019/0254345 A1 | 8/2019 | Hepworth et al. |
| 2019/0254346 A1 | 8/2019 | Hepworth et al. |
| 2019/0343182 A1 | 11/2019 | Yilmaz |
| 2020/0060333 A1 | 2/2020 | Sutton et al. |
| 2020/0367561 A1 | 11/2020 | Yilmaz et al. |
| 2020/0376208 A1 * | 12/2020 | Spencer ............ A61M 15/0003 |
| 2020/0383379 A1 | 12/2020 | Yilmaz |

(56) References Cited

U.S. PATENT DOCUMENTS

| | | | |
|---|---|---|---|
| 2020/0390157 A1* | 12/2020 | Hepworth | A24F 40/30 |
| 2020/0390158 A1* | 12/2020 | Hepworth | H05B 6/105 |
| 2021/0100284 A1 | 4/2021 | Yilmaz et al. | |
| 2021/0322687 A1* | 10/2021 | Buchberger | A61M 11/042 |

FOREIGN PATENT DOCUMENTS

| | | |
|---|---|---|
| AU | 2013214984 A1 | 8/2014 |
| AU | 2013214987 A1 | 8/2014 |
| AU | 2013214991 A1 | 8/2014 |
| AU | 2013214993 A1 | 8/2014 |
| AU | 2013214994 A1 | 8/2014 |
| AU | 2013214997 A1 | 8/2014 |
| AU | 2013214998 A1 | 8/2014 |
| CA | 2845090 A1 | 2/2013 |
| CA | 2862105 A1 | 8/2013 |
| CA | 2862294 A1 | 8/2013 |
| CA | 2863185 A1 | 8/2013 |
| CA | 2863189 A1 | 8/2013 |
| CA | 2867620 A1 | 8/2013 |
| CA | 2867624 A1 | 8/2013 |
| CA | 2868313 A1 | 8/2013 |
| CA | 2980426 A1 | 10/2016 |
| CN | 2262810 Y | 9/1997 |
| CN | 2686350 Y | 3/2005 |
| CN | 2760984 Y | 3/2006 |
| CN | 101141892 A | 3/2008 |
| CN | 201108029 Y | 9/2008 |
| CN | 101277621 A | 10/2008 |
| CN | 201238609 Y | 5/2009 |
| CN | 101951796 A | 1/2011 |
| CN | 102258219 A | 11/2011 |
| CN | 102595943 A | 7/2012 |
| CN | 102781266 A | 11/2012 |
| CN | 103263083 A | 8/2013 |
| CN | 203369383 U | 1/2014 |
| CN | 203369386 U | 1/2014 |
| CN | 103859605 A | 6/2014 |
| CN | 203801735 U | 9/2014 |
| CN | 2038010735 | 9/2014 |
| CN | 104146352 A | 11/2014 |
| CN | 104219973 A | 12/2014 |
| CN | 104244749 A | 12/2014 |
| CN | 104244750 A | 12/2014 |
| CN | 104284606 A | 1/2015 |
| CN | 104287098 A | 1/2015 |
| CN | 104302197 A | 1/2015 |
| CN | 204104830 U | 1/2015 |
| CN | 104394722 A | 3/2015 |
| CN | 204191582 U | 3/2015 |
| CN | 204275207 U | 4/2015 |
| CN | 104661544 A | 5/2015 |
| CN | 204560971 U | 8/2015 |
| CN | 104968225 A | 10/2015 |
| CN | 204812043 U | 12/2015 |
| CN | 204812045 U | 12/2015 |
| CN | 204812046 U | 12/2015 |
| CN | 204812048 U | 12/2015 |
| CN | 204812049 U | 12/2015 |
| CN | 204888735 U | 12/2015 |
| CN | 105852229 A | 8/2016 |
| CN | 205492620 U | 8/2016 |
| CN | 106490692 A | 3/2017 |
| DE | 2548019 A1 | 5/1976 |
| DE | 3938634 A1 | 6/1990 |
| DE | 19645563 A1 | 5/1998 |
| DE | 102005016415 A1 | 11/2006 |
| EA | 201290586 A1 | 12/2012 |
| EA | 201490448 A1 | 12/2014 |
| EP | 0305788 A1 | 3/1989 |
| EP | 0317154 A1 | 5/1989 |
| EP | 0336458 A2 | 10/1989 |
| EP | 0430559 A2 | 6/1991 |
| EP | 0653898 A2 | 5/1995 |
| EP | 0914021 A2 | 5/1999 |
| EP | 1609376 A1 | 12/2005 |
| EP | 1555899 B1 | 12/2006 |
| EP | 1859694 A1 | 11/2007 |
| EP | 2083643 A1 | 8/2009 |
| EP | 2316286 A1 | 5/2011 |
| EP | 2327318 A1 | 6/2011 |
| EP | 2468117 A1 | 6/2012 |
| EP | 2723429 A1 | 4/2014 |
| EP | 2727619 A2 | 5/2014 |
| EP | 2740506 A1 | 6/2014 |
| EP | 2740507 A1 | 6/2014 |
| EP | 2740508 A1 | 6/2014 |
| EP | 2727619 A3 | 7/2014 |
| EP | 2756859 A1 | 7/2014 |
| EP | 2756860 A1 | 7/2014 |
| EP | 2809180 A1 | 12/2014 |
| EP | 2809182 A2 | 12/2014 |
| EP | 2809183 A1 | 12/2014 |
| EP | 2809184 A1 | 12/2014 |
| EP | 2809185 A1 | 12/2014 |
| EP | 2809186 A1 | 12/2014 |
| EP | 2809187 A1 | 12/2014 |
| EP | 2723429 A4 | 4/2015 |
| EP | 2809180 A4 | 7/2015 |
| EP | 2809184 A4 | 7/2015 |
| EP | 2809187 A4 | 7/2015 |
| EP | 2809182 A4 | 8/2015 |
| EP | 2809183 A4 | 8/2015 |
| EP | 2809185 A4 | 8/2015 |
| EP | 2809186 A4 | 9/2015 |
| EP | 2948006 A1 | 12/2015 |
| EP | 2964038 A1 | 1/2016 |
| EP | 2975956 A1 | 1/2016 |
| EP | 2989912 A1 | 3/2016 |
| EP | 3039972 A1 | 7/2016 |
| EP | 3061358 A1 | 8/2016 |
| EP | 3100621 A1 | 12/2016 |
| EP | 3245885 A1 | 11/2017 |
| GB | 607728 A | 9/1948 |
| GB | 2299012 A | 9/1996 |
| GB | 2446440 A | 8/2008 |
| GB | 2504075 A | 1/2014 |
| GB | 2504076 A | 1/2014 |
| GB | 201413018 | 9/2014 |
| GB | 201413019 | 9/2014 |
| GB | 201413021 | 9/2014 |
| GB | 201413025 | 9/2014 |
| GB | 201413027 | 9/2014 |
| GB | 201413028 | 9/2014 |
| GB | 201413030 | 9/2014 |
| GB | 201413032 | 9/2014 |
| GB | 201413034 | 9/2014 |
| GB | 201413036 | 9/2014 |
| GB | 201413037 | 9/2014 |
| GB | 2513061 A | 10/2014 |
| GB | 2523585 A | 9/2015 |
| GB | 2523585 A8 | 9/2015 |
| GB | 2524856 A | 10/2015 |
| GB | 2525080 A | 10/2015 |
| GB | 2525294 A | 10/2015 |
| GB | 2525295 A | 10/2015 |
| GB | 2525480 A | 10/2015 |
| GB | 2525722 A | 11/2015 |
| GB | 2525723 A | 11/2015 |
| GB | 2525724 A | 11/2015 |
| GB | 2525725 A | 11/2015 |
| GB | 2525726 A | 11/2015 |
| GB | 2525727 A | 11/2015 |
| GB | 2529919 A | 3/2016 |
| GB | 2531633 A | 4/2016 |
| HK | 1197203 A1 | 1/2015 |
| HK | 1198138 A1 | 3/2015 |
| HK | 1198142 A1 | 3/2015 |
| HK | 1198143 A1 | 3/2015 |
| HK | 1200128 A1 | 7/2015 |
| HK | 1200129 A1 | 7/2015 |
| HK | 1203128 A1 | 10/2015 |
| IL | 233651 | 8/2014 |
| IL | 233896 | 9/2014 |

(56) References Cited

FOREIGN PATENT DOCUMENTS

| | | |
|---|---|---|
| IL | 230930 A | 6/2017 |
| IL | 233851 A | 6/2019 |
| IL | 233653 A | 4/2020 |
| IL | 233885 A | 5/2020 |
| IL | 233894 A | 5/2020 |
| IL | 233895 A | 5/2020 |
| JP | S5736898 U | 2/1982 |
| JP | S6033891 U | 3/1985 |
| JP | S649598 U | 1/1989 |
| JP | H0198470 A | 4/1989 |
| JP | H022331 A | 1/1990 |
| JP | H07192906 A | 7/1995 |
| JP | 3192677 B2 | 7/2001 |
| JP | 3325028 B2 | 9/2002 |
| JP | 3392138 B2 | 3/2003 |
| JP | 2006503572 A | 2/2006 |
| JP | 2006504431 A | 2/2006 |
| JP | 4324276 B2 | 9/2009 |
| JP | 2009213428 A | 9/2009 |
| JP | 2010506594 A | 3/2010 |
| JP | 2012075370 A | 4/2012 |
| JP | 2012135299 A | 7/2012 |
| JP | 2013509160 A | 3/2013 |
| JP | 2013519384 A | 5/2013 |
| JP | 2014524313 A | 9/2014 |
| JP | 2014532433 A | 12/2014 |
| JP | 2015503335 A | 2/2015 |
| JP | 2015505474 A | 2/2015 |
| JP | 2015505475 A | 2/2015 |
| JP | 2015505476 A | 2/2015 |
| JP | 2015506182 A | 3/2015 |
| JP | 2015508641 A | 3/2015 |
| JP | 2015512617 A | 4/2015 |
| JP | 2015513393 A | 5/2015 |
| JP | 2015513909 A | 5/2015 |
| JP | 2015516809 A | 6/2015 |
| JP | 2016509852 A | 4/2016 |
| JP | 2016517701 A | 6/2016 |
| JP | 2017511703 A | 4/2017 |
| JP | 2017512470 A | 5/2017 |
| KR | 20140070543 A | 6/2014 |
| KR | 20140090138 A | 7/2014 |
| KR | 20140125822 A | 10/2014 |
| KR | 20140125827 A | 10/2014 |
| KR | 20140125828 A | 10/2014 |
| KR | 20140125829 A | 10/2014 |
| KR | 20140127288 A | 11/2014 |
| KR | 20150003845 A | 1/2015 |
| KR | 20150005514 A | 1/2015 |
| KR | 20150018515 A | 2/2015 |
| KR | 20150035488 A | 4/2015 |
| MA | 20150054 A1 | 2/2015 |
| MA | 20150055 A1 | 2/2015 |
| MA | 20150056 A1 | 2/2015 |
| MA | 20150057 A1 | 2/2015 |
| MA | 20150058 A1 | 2/2015 |
| MA | 20150153 A1 | 5/2015 |
| MA | 20150169 A1 | 6/2015 |
| MX | 2014009396 A | 2/2015 |
| MX | 2014009398 A | 2/2015 |
| MX | 2014009393 A | 5/2015 |
| MX | 2014009394 A | 5/2015 |
| MX | 2014009397 A | 5/2015 |
| NZ | 627439 A | 9/2015 |
| NZ | 628058 A | 1/2016 |
| RU | 2015111364 A | 9/2015 |
| RU | 157882 U1 | 12/2015 |
| RU | 2581999 C2 | 4/2016 |
| RU | 2602964 C2 | 11/2016 |
| SG | 2014013627 A | 7/2014 |
| TW | 201315397 A | 4/2013 |
| WO | WO-9406314 A1 | 3/1994 |
| WO | WO-9527412 A1 | 10/1995 |
| WO | WO-02069745 A1 | 9/2002 |
| WO | WO-2004089126 A1 | 10/2004 |
| WO | WO-2006098171 A1 | 9/2006 |
| WO | WO-2007110650 A1 | 10/2007 |
| WO | WO-2009022232 A2 | 2/2009 |
| WO | WO-2010045671 A1 | 4/2010 |
| WO | WO-2011095410 A1 | 8/2011 |
| WO | WO-2011101164 A1 | 8/2011 |
| WO | WO-2012117578 A1 | 9/2012 |
| WO | WO-2012156695 A1 | 11/2012 |
| WO | WO-2013020280 A1 | 2/2013 |
| WO | WO-2013025921 A1 | 2/2013 |
| WO | WO-2013034459 A1 | 3/2013 |
| WO | WO-2013068081 A1 | 5/2013 |
| WO | WO-2013068100 A1 | 5/2013 |
| WO | WO-2013098405 A2 | 7/2013 |
| WO | WO-2013110211 A1 | 8/2013 |
| WO | WO-2013116558 A1 | 8/2013 |
| WO | WO-2013116561 A1 | 8/2013 |
| WO | WO-2013116565 A1 | 8/2013 |
| WO | WO-2013116567 A1 | 8/2013 |
| WO | WO-2013116568 A2 | 8/2013 |
| WO | WO-2013116571 A1 | 8/2013 |
| WO | WO-2013116572 A1 | 8/2013 |
| WO | WO-2013120566 A2 | 8/2013 |
| WO | WO-2013121608 A1 | 8/2013 |
| WO | WO-2013138384 A2 | 9/2013 |
| WO | WO-2013138384 A3 | 10/2013 |
| WO | WO-2013148810 A1 | 10/2013 |
| WO | WO-2013151295 A1 | 10/2013 |
| WO | WO-2013155645 A1 | 10/2013 |
| WO | WO-2013156339 A1 | 10/2013 |
| WO | WO-2013179524 A1 | 12/2013 |
| WO | WO-2014012905 A1 | 1/2014 |
| WO | WO-2014048745 A1 | 4/2014 |
| WO | WO-2014085719 A1 | 6/2014 |
| WO | WO-2014116974 A1 | 7/2014 |
| WO | WO-2014139611 A1 | 9/2014 |
| WO | WO-2014140273 A2 | 9/2014 |
| WO | WO-2014158051 A1 | 10/2014 |
| WO | WO-2013116568 A3 | 11/2014 |
| WO | WO-2014184239 A1 | 11/2014 |
| WO | WO-2015013108 A2 | 1/2015 |
| WO | WO-2015013108 A3 | 4/2015 |
| WO | WO-2015047954 A1 | 4/2015 |
| WO | WO-2015108816 A2 | 7/2015 |
| WO | WO-2015128665 A1 | 9/2015 |
| WO | WO-2015128666 A1 | 9/2015 |
| WO | WO-2015128667 A1 | 9/2015 |
| WO | WO-2016024083 A1 | 2/2016 |
| WO | WO-2016050244 A1 | 4/2016 |
| WO | WO-2016062777 A1 | 4/2016 |
| WO | WO-2016076178 A1 | 5/2016 |
| WO | WO-2016090426 A1 | 6/2016 |
| WO | WO-2016121143 A1 | 8/2016 |
| WO | WO-2016135342 A2 | 9/2016 |
| WO | WO-2016178377 A1 | 11/2016 |
| WO | WO-2016208759 A1 | 12/2016 |
| WO | WO-2017055514 A1 | 4/2017 |
| WO | WO-2017149152 A1 | 9/2017 |
| WO | WO-2017160559 A1 | 9/2017 |
| WO | WO-2017185051 A1 | 10/2017 |
| WO | WO-2018083037 A1 * | 5/2018 ............. A24B 13/00 |
| WO | WO-2018127417 A1 * | 7/2018 ............. A24F 40/10 |
| WO | WO-2019081571 A1 | 5/2019 |

OTHER PUBLICATIONS

Application and File History for U.S. Appl. No. 16/475,571, filed Jul. 2, 2019, inventor Yilmaz.

Communication pursuant to Article 94(3) EPC for Application No. 1778008.3, dated Sep. 11, 2020, 8 pages.

Communication pursuant to Article 94(3) EPC for Application No. 17835844.6, dated Nov. 25, 2020, 5 pages.

Decision to Grant for Japanese Application No. 2015-559560, dated Apr. 4, 2017, 3 pages (6 pages with translation).

Decision to Grant dated Oct. 22, 2020 for Russian Application No. 2020118485, 9 pages.

Examination Report for New Zealand for Application No. 764845, dated Nov. 17, 2021, 4 pages.

(56) References Cited

OTHER PUBLICATIONS

Examination Report dated Oct. 26, 2017 for European Application No. 14717683.8, 5 pages.
Extended European Search Report for Application No. 18210216.0, dated May 9, 2019, 8 pages.
Extended European Search Report for Application No. 20210790.0, dated Feb. 18, 2021, 7 pages.
International Preliminary Report on Patentability for Application No. PCT/GB2014/050544, dated Sep. 11, 2015, 6 pages.
International Preliminary Report on Patentability for Application No. PCT/EP2017/073057, dated Mar. 28, 2019, 9 pages.
International Preliminary Report on Patentability for Application No. PCT/EP2017/072811, dated Aug. 20, 2018, 7 pages.
International Preliminary Report on Patentability for Application No. PCT/EP2017/072814, dated Nov. 30, 2018, 8 pages.
International Preliminary Report on Patentability for Application No. PCT/EP2018/083665, dated Mar. 27, 2020, 15 pages.
International Preliminary Report on Patentability for Application No. PCT/GB2014/050545, dated Feb. 27, 2015, 5 pages.
International Preliminary Report on Patentability for Application No. PCT/EP2017/072813, dated Nov. 30, 2018, 9 pages.
International Preliminary Report on Patentability for Application No. PCT/EP2017/083785, dated Mar. 26, 2019, 17 pages.
International Preliminary Report on Patentability for Application No. PCT/EP2014/055485, dated Oct. 1, 2015, 11 pages.
International Preliminary Report on Patentability for Application No. PCT/EP2017/073061, dated Mar. 28, 2019, 7 pages.
International Preliminary Report on Patentability for Application No. PCT/EP2017/083784, dated Apr. 8, 2019, 23 pages.
International Search Report and Written Opinion for Application No. PCT/EP2014/055485, dated Jul. 31, 2014, 16 pages.
International Search Report and Written Opinion for Application No. PCT/EP2017/072811, dated Dec. 11, 2017, 15 pages.
International Search Report and Written Opinion for Application No. PCT/EP2017/072813, dated Dec. 11, 2017, 12 pages.
International Search Report and Written Opinion for Application No. PCT/EP2017/072814, dated Dec. 11, 2017, 12 pages.
International Search Report and Written Opinion for Application No. PCT/EP2017/073057, dated Feb. 7, 2018, 16 pages.
International Search Report and Written Opinion for Application No. PCT/EP2017/073061, dated Jan. 8, 2018, 13 pages.
International Search Report and Written Opinion for Application No. PCT/EP2017/083784, dated Jun. 20, 2018, 20 pages.
International Search Report and Written Opinion for Application No. PCT/EP2017/083785, dated Apr. 9, 2018, 14 pages.
International Search Report and Written Opinion for Application No. PCT/GB2014/050544, dated Sep. 22, 2014, 7 pages.
International Search Report and Written Opinion for Application No. PCT/GB2014/050545, dated Oct. 8, 2014, 9 pages.
International Search Report for Application No. PCT/EP2018/083665, dated Mar. 13, 2019, 5 pages.
International Search Report for Application No. PCT/EP2019/053821, dated May 24, 2019, 3 pages.
International Search Report for Application No. PCT/EP2019/053822, dated May 24, 2019, 3 pages.
Korean Office Action dated Oct. 26, 2020 for Korean Application No. 10-2019-7010642 27 pages.
Korean Office Action dated Oct. 26, 2020 for Korean Application No. 10-2019-7010644, 21 pages.

Notice of Allowance for Japanese Application No. 2015-559560, dated Mar. 27, 2017, 3 pages.
Notice of Reasons for Rejection for Japanese Application No. 2019-535975, dated Jul. 7, 2020, 9 pages.
Notification to Grant Patent Right for Invention of Chinese Application No. 201480023894.4, dated Dec. 4, 2017, 5 pages.
Office Action dated Sep. 30, 2019 for Chinese Application No. 201480017532.4 filed Mar. 19, 2014, 20 pages.
Office Action dated Sep. 8, 2020 for Japanese Application No. 2019-531421, filed Dec. 20, 2017, 16 pages.
Office Action for Chinese Application No. 201480023874.7, dated Mar. 30, 2018, 11 pages.
Office Action for Chinese Application No. 201480023894.4, dated Dec. 8, 2016, 8 pages.
Office Action for Chinese Application No. 2019-531415, dated Oct. 6, 2020, 12 pages.
Office Action for Japanese Application No. 2015-559559, dated Nov. 29, 2016, 4 pages (8 pages with translation).
Office Action for Japanese Application No. 2015-559560, dated Sep. 13, 2016, 4 pages (7 pages with translation).
Office Action for Japanese Application No. 2019-531421, dated Feb. 9, 2021, 14 pages.
Office Action For Japanese Application No. 2020-529231, dated Jul. 20, 2021, 4 pages.
Office Action For Korean Application No. 10-2019-7010649, dated Jan. 19, 2021, 7 pages.
Office action for Korean Application No. 10-2020-7016127, dated Apr. 29, 2022, 26 pages.
Office Action dated Jan. 11, 2017 for Korean Application No. 10-2015-7025842, 25 pages (67 pages with translation).
Office Action dated Dec. 18, 2018 for Japanese Application No. 2017-172628, 4 pages.
Office Action dated Feb. 19, 2020 for Russian Patent Application No. 2019125438, 21 pages.
Office Action dated Aug. 20, 2020 for Russian Application No. 2019107330, 13 pages.
Office Action dated Jul. 21, 2020 for European Application No. 17780009.1, 7 pages.
Office Action dated Jul. 21, 2020 for Japanese Application No. 2019-513761, 11 pages.
Office Action dated Jul. 21, 2020 for Japanese Application No. 2019-513827, 9 pages.
Office Action dated Jul. 21, 2020 for Japanese Application No. 2019-513842, 11 pages.
Office Action dated Dec. 22, 2020 for Korean Application No. 10-2019-7023118, 20 pages.
Office Action dated Aug. 23, 2016 for Japanese Application No. 2016-503647, 3 pages.
Office Action dated Jul. 7, 2020 for Japanese Application No. JP2019-513828, 12 pages.
Search report dated Sep. 23, 2019 for Chinese Application No. 201480017532.4 filed Mar. 19, 2014, 2 pages.
Search Report dated Mar. 2, 2018 for Great Britain Application No. GB1615609.3, 4 pages.
Written Opinion for Application No. PCT/EP2019/053821, dated May 24, 2019, 6 pages.
Written Opinion for Application No. PCT/EP2019/053822, dated May 24, 2019, 6 pages.
Ye Zonglin., "Household Electric Appliance Introduction," Light Industry Press, Mar. 1983, First Edition, pp. 74-78.

* cited by examiner

COMPONENT FOR AN AEROSOL-GENERATING APPARATUS

TECHNICAL FIELD

The present invention relates to aerosol generation, and more particularly to an aerosol generating apparatus and a component for an aerosol generating apparatus.

BACKGROUND

Smoking articles such as cigarettes, cigars and the like burn tobacco during use to create tobacco smoke. Attempts have been made to provide alternatives to these articles that burn tobacco by creating products that release compounds without burning.

Examples of such products are heating devices which release compounds by heating, but not burning, the material. The material may be for example tobacco or other non-tobacco products, which may or may not contain nicotine.

As another example, there are so-called e-cigarette devices. These devices typically contain a liquid which is heated to vaporise the liquid to produce an inhalable vapour or aerosol. The liquid may contain nicotine and/or flavourings and/or aerosol-generating substances, such as glycerol. The known e-cigarette devices typically do not contain or use tobacco.

As yet another example, there are so-called hybrid devices. These hybrid devices typically contain separately a liquid and tobacco or other flavour material. The liquid is heated to vaporise the liquid to produce an inhalable vapour or aerosol which passes through the tobacco or other flavour material so that a flavour is imparted to the vapour or aerosol.

SUMMARY

According to a first aspect of the present invention, there is provided a component for an aerosol-generating apparatus, the component comprising: a liquid container for containing liquid; a wick arranged to draw liquid from the liquid container in use; and a heater arranged to volatilise liquid drawn from the liquid container by the wick in use to generate an aerosol in use; wherein the heater defines a channel for receiving a material element for modifying a property of the aerosol generated in use; wherein the component is arranged such that, in use, the material element received in the channel in use modifies the property of the aerosol generated in use thereby to generate a modified aerosol for inhalation by a user.

Optionally, in use, the aerosol generated in use passes through the material element received in the channel in use thereby to modify the property of the aerosol to generate the modified aerosol.

Optionally, the heater comprises a heating element substantially coiled around the channel.

Optionally, the wick substantially surrounds the heater along a length of the heater.

Optionally, the wick and the heater are provided by a porous ceramic heater.

Optionally, the liquid container substantially surrounds the wick along a length of the wick.

Optionally, the channel extends in a direction parallel to a length of the component.

Optionally, two or more of the liquid container, the wick, the heater, and the channel are substantially concentric and/or coaxial.

Optionally, one or both of the wick and the liquid container are annular in shape.

Optionally, the heater is arranged to heat the material element received in the channel in use directly.

Optionally, the component comprises a receptacle for receiving therein the material element, the receptacle being configured to be received in the channel.

Optionally, the receptacle comprises a mesh for containing the material element and for allowing aerosol generated in use to pass therethrough.

Optionally, the receptacle is removable from the channel.

Optionally, the receptacle has a mouthpiece connected thereto, the mouthpiece defining an outlet for allowing the modified aerosol to be inhaled by a user.

Optionally, the mouthpiece is removably connected to the receptacle.

Optionally, the component comprises the material element received in the channel.

Optionally, the material element is received in the receptacle.

Optionally, the material element is arranged to modify one or more organoleptic properties of the aerosol generated in use.

Optionally, the material element is or comprises tobacco.

Optionally, the component is a cartridge for the aerosol generating apparatus.

According to a second aspect of the present invention, there is provided an aerosol-generating apparatus comprising the component according to the first aspect.

Optionally, the aerosol-generating device comprises a battery portion arranged to provide electrical power to the heater.

According to a third aspect of the present invention, there is provided an aerosol-generating apparatus comprising: a liquid container for containing liquid; a wick arranged to draw liquid from the liquid container in use; and a heater arranged to volatilise liquid drawn from the liquid container by the wick in use to generate an aerosol in use, wherein the heater defines a channel for receiving a material element for modifying a property of said aerosol generated in use; wherein the apparatus is arranged such that, in use, the material element received in the channel in use modifies a said property of the aerosol generated in use thereby to generate a modified aerosol for inhalation by a user.

According to a fourth aspect of the present invention, there is provided a method of generating a modified aerosol for inhalation by a user, the method comprising: volatilising, by a heater, liquid drawn in from a liquid container by a wick, thereby to generate an aerosol; and modifying, by a material element received in a channel defined by the heater, a property of the aerosol, thereby to generate the modified aerosol for inhalation by a user.

Optionally, the modifying the property of the aerosol comprises passing the aerosol through the material element received in the channel defined by the heater.

Further features and advantages of the invention will become apparent from the following description of preferred embodiments of the invention, given by way of example only, which is made with reference to the accompanying drawings.

DETAILED DESCRIPTION

Figure 1:
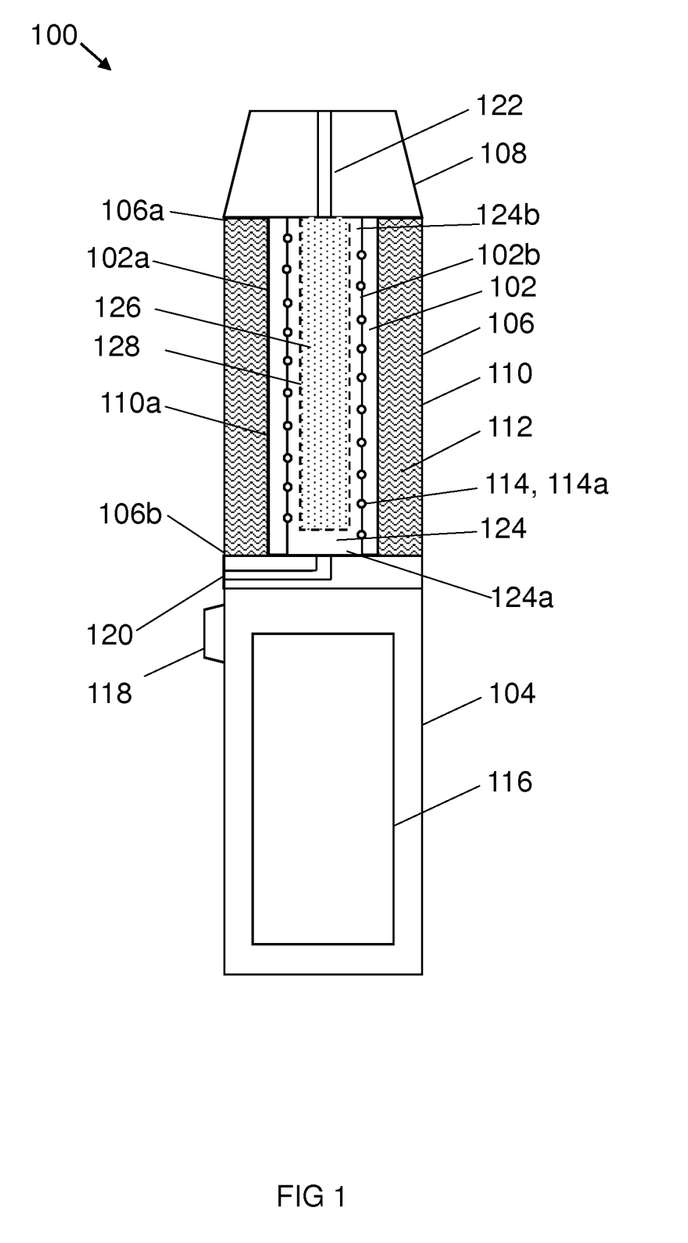
FIG. 1 illustrates schematically a sectional view of an aerosol generating apparatus according to an example.
Figure 2:
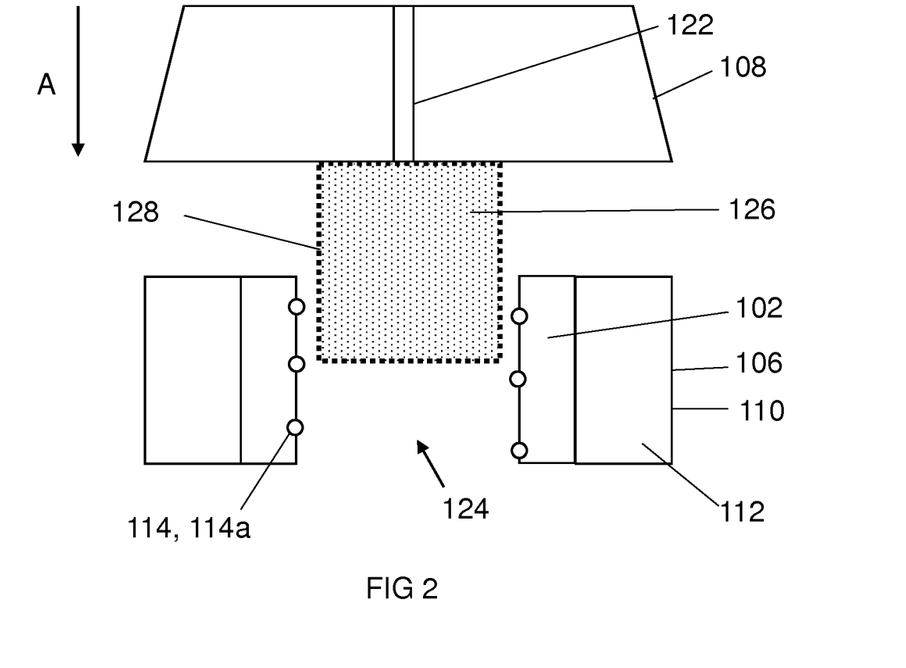
FIG. 2 illustrates schematically a sectional view of a portion of the aerosol generating apparatus of the example of FIG. 1, but in a different configuration.
Figure 3:
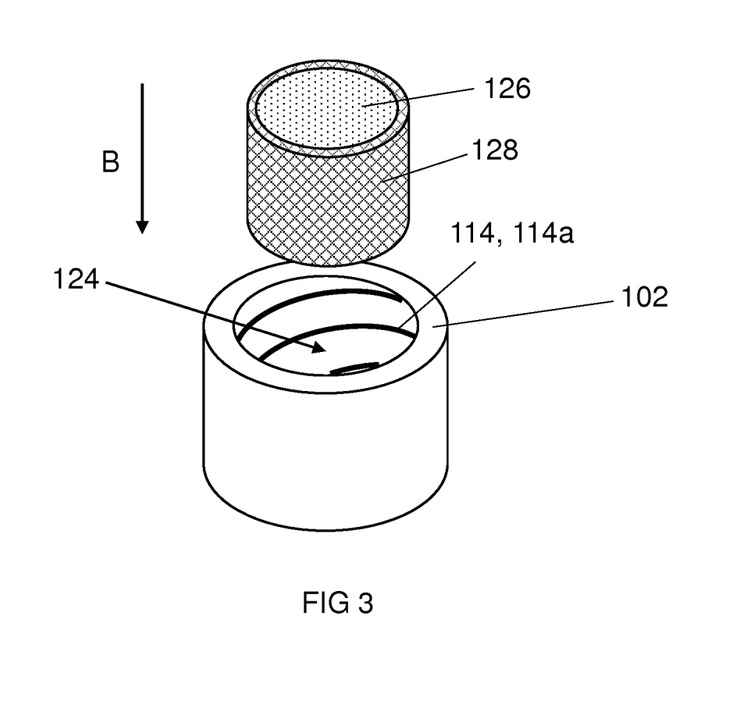
FIG. 3 illustrates schematically a perspective view of a portion of the aerosol generating apparatus of the example of FIG. 1, but in a different configuration.

FIG. 1 illustrates schematically a sectional view of an aerosol generating apparatus 100 according to an example. FIGS. 2 and 3 illustrate portions of the apparatus 100, in different configurations. In broad outline, the apparatus 100 volatilises a liquid 112 to generate a flow of vapour or aerosol, which contacts and/or passes through a material element 126 to modify a property of the vapour or aerosol. An inhalable medium may thereby be produced.

In this respect, first it may be noted that, in general, a vapour is a substance in the gas phase at a temperature lower than its critical temperature, which means that for example the vapour can be condensed to a liquid by increasing its pressure without reducing the temperature. On the other hand, in general, an aerosol is a colloid of fine solid particles or liquid droplets, in air or another gas. A "colloid" is a substance in which microscopically dispersed insoluble particles are suspended throughout another substance. For brevity, in the following, the term "aerosol" is used to refer to one or both of "vapour" and "aerosol".

Returning to FIGS. 1 to 3, as best seen in FIG. 1, the apparatus 100 is a generally elongate apparatus. The apparatus 100 is hand-held. The apparatus 100 comprises a battery portion 104, a component 106, and a mouthpiece 108.

The component 106 of the apparatus 100 is in this example a cartridge 106 for use with the aerosol generating apparatus 100. The cartridge 106 may be disposable, i.e. intended to be disposed of once spent and, for example replaced with a replacement cartridge 106. The cartridge 106 comprises a liquid container 110 containing liquid 112, a wick 102 arranged to draw the liquid 112 from the liquid container 110, and a heater 114 arranged to volatilise liquid 112 drawn from the liquid container 110 by the wick 102 to generate a flow of aerosol in use. It will be appreciated that in other examples (not illustrated) the component 106 need not necessarily be a cartridge 106, for example a disposable cartridge 106, for an aerosol generating apparatus 100, and may instead be for example an integral component 106 of the aerosol generating apparatus 100, or may for example be a separable but nonetheless non-disposable, for example at least partially reusable, component of the aerosol generating apparatus 100.

Returning to the illustrated example, the liquid container 110 is annular in shape. The liquid container 110 contains or holds the liquid 112 during operation of the aerosol generating apparatus 100. The liquid 112 may be, for example, liquid 112 which when heated may be volatilised to produce an aerosol. The liquid 112 may be liquid 112 that is volatilisable at reasonable temperatures, for example in the range of 100-300° C. or in the range of 150-250° C. Suitable liquids may be or comprise, for example, propylene glycol and/or glycerol (also known as glycerine). The liquid 112 may comprise one or more flavourants and/or nicotine. The liquid container 110 may be arranged to allow refilling of the liquid container 110 with liquid 112. For example, the liquid container 110 may comprise an access portion (not shown) to allow a user to refill the liquid container 110 with liquid 112 when desired. Alternatively, the liquid container 110 may be sealed such that once the liquid 112 is consumed then the cartridge 106 is intended to be disposed of and a replacement cartridge 106 used.

The wick 102 is generally absorbent. The wick 102 is arranged to draw the liquid 112 from the liquid container 110, for example by capillary action. The wick 102 may be non-woven and may be for example a cotton or wool material or the like, or a synthetic material, including for example polyester, nylon, viscose, polypropylene or the like, or a ceramic material. The liquid container 110 substantially surrounds the wick 102 along a length of the wick 102. The wick 102 is annular in shape. In this example, the wick 102 is substantially circumscribed by the liquid container 110 along the length of the wick 102. An outer cylindrical surface 102a of the wick 102 is in contact with the liquid 112 held in the liquid container 110 and acts to draw the liquid 112 in towards an inner cylindrical surface 102b of the wick 102, where the heater 114 is positioned. In some examples, the outer surface 102a of the wick may partially define the liquid container 110. In other examples, an inner surface 110a of the liquid container 110 may be porous, and the wick 102 may contact the porous inner surface 110a of the liquid container 110 so as to draw, by capillary action, liquid 112 held in the liquid container 110, through the porous inner surface 110a of the liquid container 110, through the wick 102, and onto the heater 114.

The heater 114 may be a resistive heater 114. The heater 114 is arranged to volatilise liquid 112 drawn from the liquid container 110 by the wick 102 to generate a flow of aerosol. The heater 114 is supported by the wick 102, and is partially embedded in the wick 102, specifically partially embedded in the inner surface 102b of the wick 102.

The cartridge 106 comprises an air inlet 120 for allowing air to be drawn towards the heater 114. The heater may volatilise the liquid 112 into air drawn in from the air inlet 120, thereby to generate the flow of aerosol.

The cartridge 106 is connected to the battery portion 104. The cartridge 106 may be removably connected to the battery portion 104, for example to allow replacement of the cartridge 106. The battery portion 104 comprises a battery 116 for providing electrical power to the heater 114. Electrical current provided by the battery 116 may pass through the heater 114, thereby to increase the temperature of the heater 114 by resistive heating. The battery portion 104 comprises a button 118 to allow a user to control the provision of electrical current from the battery 116 to the heater 114, and hence allow control of the generation of aerosol by the heater 114.

The mouthpiece 108 is connected to the cartridge 106. For example, the mouthpiece 108 may be removably connected to the cartridge 106. The mouthpiece 108 is connected to the cartridge 106 at an opposite end 106a of the cartridge to the end 106b to which the battery portion 104 is connected. The mouthpiece 108 defines an outlet 122 for allowing aerosol generated by the heater 114 to be drawn from the apparatus 100.

The heater 114 defines a channel 124. The channel 124 is substantially cylindrical. The channel 124 is elongate and substantially circular in cross section. The channel 124 extends through the heater 114. The channel 124 extends in a direction substantially parallel to the length of the cartridge 106, and of the overall apparatus 100. The channel 124 is located substantially centrally of the heater 114. In this example, the channel 124 extends from a first open end 124a proximate to the battery portion 104 to a second open end 124b proximate to the mouthpiece 108. Air drawn in from the air inlet 120 passes into the first open end 124a of the channel 124, and modified aerosol, i.e. aerosol having passed through or contacted the material element 126, exits the second open end 124b of the channel 124 into the outlet 122 defined by the mouthpiece 108. A diameter of the channel 124 may be in the range of from 10 mm to 20 mm, for example from 10 mm to 16 mm or from 15 mm to 20 mm. It will be appreciated that the channel 124 need not necessarily be open at both of its ends 124a, 124b, and that in some examples (not shown) the first end 124a of the channel 124 for example may be substantially closed and the air inlet 120 may be in fluid communication with a portion of the channel 124 at or towards the closed first end 124a.

The heater 114 substantially surrounds the channel 124 along the length of the channel 124. A volume bounded by the heater 114, for example a heating element 114a of the heater 114, may constitute a part or a whole of the channel 124. In this example, the heater 114 is a coil heater 114. The coil heater 114 comprises a heating element 114a arranged around the channel 124. As perhaps best seen in FIG. 3, the heating element 114a is coiled around the channel 124. Specifically, the heating element 114a is a resistively heated wire 114a arranged around the channel 124 in a helical arrangement. The coiled heating element 114a extends in a direction parallel to the length of cartridge 106 and/or overall apparatus 100, and may be referred to as a vertical heating coil arrangement 114. In this example, the coiled heating element 114 extends along substantially the entire length of the cartridge 106. The heating element 114a may at least partially define the channel 124, i.e. the volume bounded by the heating element 114a may constitute a part or the whole of the channel 124. The heating element 114a may be supported by the wick, for example partially embedded in the wick 102.

The channel 124 has received therein a material element 126. The material element 126 is received within the channel 124 that is defined by the heater 114. As the skilled person will appreciate, in this example, the material element 126 is therefore received within the heater 114; in this example, substantially entirely within the heater 114. In this case, substantially the entire length of material element 126 may be heated by the heater 114 in use. The material element 126 is received generally centrally of the heater 114. The heater 114 substantially surrounds the material element 126 along the length of the material element 126.

In the example illustrated in FIGS. 1 to 3, the material element 126 is received in a receptacle 128. The receptacle 128 is received in the channel 124 defined by the heater 114. As perhaps best seen in FIGS. 2 and 3, the receptacle 128 is removeable from the channel 124 (see for example FIG. 2 where the receptacle 128 is partially removed from the channel 124, and FIG. 3 where the receptacle 128 is fully removed from the channel 124). This may allow a user to change the material element 126 received in the receptacle 128, for example to replace the material element 126 when needed, or for example to change a flavour type of the material element 126. The receptacle 128 defines one or more apertures for allowing aerosol generated to pass therethrough. For example, the receptacle 128 may define an array of apertures around an outer circumference of the receptacle 128. For example, the receptacle 128 may comprise a mesh for containing the material element 126 and for allowing aerosol to pass therethrough. The receptacle 128 is substantially cylindrical, and is dimensioned for a close fit in the cylindrical channel 124. The receptacle 128 extends along the length of the channel 124. The heater 114 substantially surrounds the receptacle 128 along a length of the receptacle 128 (and hence the material element 126 received therein). The heater 114 is adjacent to the receptacle 128. A diameter of the receptacle 128 (i.e. the diameter to the outer surface of the receptacle may be, for example, in the range of from 9 mm to 20 mm, for example in the range of from 9 mm to 15 mm or from 14 mm to 19 mm.

In this example, the receptacle 128 is connected to the mouthpiece 108. The mouthpiece 108 is arranged so that the outlet 122 allows aerosol, having contacted or passed through the material element 126 received in the receptacle 128, to be inhaled by a user. As perhaps best seen in FIG. 2, in this example, the mouthpiece 108 and the receptacle 128 containing the material element 126 may be inserted, removed, and/or replaced from the cartridge 106 as a single piece. The mouthpiece 108 and the receptacle 128 containing the material element 126 may therefore be thought of together as a consumable. For example, a user may insert the receptacle 128 having received therein the material element 126 into the channel 124 (see, for example, arrow A of FIG. 2), and then connect the mouthpiece 108 to the upper end 106a of the cartridge 106, for example, via a snap fit connection or a screw fit connection provided therebetween (not shown), thereby to install the material element 126 into the channel 124. The mouthpiece 108 is connected to the receptacle 128 such that when the mouthpiece 108 is removed from the cartridge 106 and/or overall apparatus 100, the receptacle 128 and the material element 126 come with it. In some examples, the mouthpiece 108 may be removably connected to the receptacle 128, for example via snap fit or screw fit, to allow a user access to the material element 126 contained in the receptacle 128. This may allow for installation, removal and/or replacement of a material element 126 in the receptacle 128. The material element 126 may therefore be thought of as a consumable.

The material element 126 is for modifying a property of aerosol passing therethrough. For example, the material element 126 may be for modifying one or more organoleptic properties, for example flavour, of aerosol passing therethrough. The material element 126 may be or comprise a material for modifying a property, for example an organoleptic property, for example flavour, of aerosol passing therethrough. The material element 126 may be or comprise a material in solid form. The material element 126 may be or comprise tobacco. For example, the material element 126 may include any tobacco-containing material and may, for example, include one or more of tobacco per se, different varieties of tobacco, tobacco derivatives, pelletised tobacco, extruded tobacco, expanded tobacco, reconstituted tobacco, ground tobacco, tobacco extract, homogenised tobacco or tobacco substitutes. The tobacco may be in the form of a rod of tobacco, a pod or plug of tobacco, loose tobacco, agglomerates, etc., and may be in relatively dry form or in relatively moist form for example. The tobacco may have been modified, for example chemically modified. For example, the tobacco may have had its pH modified so as to promote the release of selected constituents of the tobacco, such as nicotine. The material element 126 may be or comprise other, non-tobacco, products or materials, which, depending on the product or material, may or may not contain nicotine. It should be noted that the material element 126 is distinct from the wick 102.

As mentioned above, in this example, the heater 114 substantially surrounds the channel 124 along a length of the channel 124, and hence substantially surrounds the material element 126 received in the channel 124 along a length of the material element 126. The wick 102 is substantially annular in shape and substantially surrounds the heater 114 along a length of the heater 114. The liquid container 110 is substantially annular in shape and substantially surrounds the wick 102 and the heater 114 along a length of the wick 102 and the heater 114. Two or more of the liquid container 110, the wick 102, the heater 114, and the channel 124 may be substantially concentric and/or coaxial. For example, each of the channel 124, the heater 114, the wick 102 and/or the liquid container 110 may be substantially concentric and/or coaxial. This may provide a space efficient arrangement.

Referring to the apparatus 100 illustrated in FIG. 1, in use, a user may draw on the mouthpiece 108, which may in turn draw air from the air inlet 120 to the channel 124. The user may operate the button 118 of the battery portion 104 so as to provide electrical power to the heater 114, and the temperature of the heater 114 may increase by resistive heating. Liquid 112 drawn from the liquid container 110 to the heater 114 by the wick 102 may be volatilised by the heater 114 to generate a flow of aerosol into the air in the channel 124. The aerosol may be drawn through the apertures in the receptacle 128, and drawn through the material element 126 received in the receptacle 128 towards the outlet 122. The material element 126 may modify a property of the aerosol passing therethrough, for example an organoleptic property of the aerosol, for example a flavour of the aerosol, thereby to generate a modified aerosol. For example, constituents of the material element 126 may be released and entrained in the aerosol passing therethrough. For example, the material element 126 may be or comprise tobacco, and the tobacco may impart a tobacco aroma and/or flavour to the aerosol passing therethrough. The modified aerosol, i.e. aerosol having passed through the material element 126 and therefore having one or more of its properties modified, may then be drawn through the outlet 122 of the mouthpiece 108, for inhalation by the user. In such a way, an inhalable medium is generated by the aerosol generating apparatus 100.

Accordingly, a method of generating a modified aerosol for inhalation by a user, for example using the cartridge 106 and/or apparatus 100 described with reference to FIGS. 1 to 3 and/or variations thereof described herein, may comprise volatilising, by the heater 114, liquid 112 drawn in from the liquid container 110 by the wick 102, to generate an aerosol; and modifying, by the material element 126 received in the channel 124 defined by the heater 114, a property of the aerosol, to generate the modified aerosol for inhalation by a user. For example, as described above, modifying the property of the aerosol may comprise passing the aerosol through the material element 126 received in the channel 124 defined by the heater 114.

The channel 124 in which the material element 126 is received being defined by the heater 114 may allow for efficient heat transfer from the heater 114 to the material element 126. For example, the heater 114 may heat the material element 126 directly, for example via radiation (in particular infrared radiation) emitted by the heater 114 (or components thereof) falling directly on the material element 126 itself. For example, in embodiments in which the material element 126 is received in receptacle 128, the heater 114 may heat the receptacle 128 and the material element 126 received therein via radiation emitted by the heater 114 (or components thereof) falling directly on the receptacle 128 (or a portion thereof), or directly on the material element 126 itself (for example via apertures in the receptacle 128). The heater 114 may alternatively or additionally heat the receptacle 128 and/or the material element 126 by thermal conduction and/or convection from the heater 114 to the receptacle 128 and/or the material element 126. The receptacle 128 may comprise good thermal conductors, for example, copper or other metals, non-metals such as graphene or other carbon-based materials, in order to promote heat transfer from the heater 114 to the material element 126. The receptacle 128, being heated by the heater 114, may in turn heat the material element 126 received therein by, for example, thermal conduction, radiation, convection, or any combination thereof. In this case, the heater 114 may heat the material element 126 via the receptacle 128.

The material element 126 being heated by the heater 114 may encourage release of constituents from the material element 126 into the aerosol. In the example that the material element 126 is or comprises tobacco, heating of the tobacco (for example above ambient temperature) increases the release of volatile constituents of the tobacco, thereby increasing the level of flavour imparted to aerosol passing therethrough. The heating of the material element 126 may therefore enhance the ability of the material element 126 to modify a property, for example flavour, of the aerosol passing therethrough. This may allow for an improved user experience. This may also allow for more efficient use of the material element 126. The heating of the material element 126 by the heater 114 that volatises the liquid 112 may reduce a need to provide a separate, dedicated heater to heat the material element 126. Thus, the electricity required to power the device may be reduced, and hence battery life may be preserved.

Moreover, close or adjacent to the heater 114, the aerosol produced may have a temperature higher than aerosol that has travelled away from the heater 114. The temperature of the aerosol adjacent to the heater may therefore be higher than the ambient temperature of the material element 126. The channel 124 in which the material element 126 is received being defined by the heater 114 may therefore allow for relatively hot aerosol to come into contact with the material element 126 and/or to pass through the material element 126, and hence allow for the aerosol to heat (for example alternatively or additionally to the heating by the heater 114 itself) the material element 126. This may improve release of constituents from the material element 126 into the aerosol passing therethrough.

The heater 114 substantially surrounding the material element 126 received in the channel 124 along a length of the material element 126 may improve heat transfer to the material element 126, as a relatively large surface area of the material element 126 (and/or receptacle 128 in which the material element 126 is received) may be exposed to the heater 114. The heating element 114a being coiled around a length of the channel 124 may allow for a substantial length of the material element 126 to be effectively and evenly heated. The wick 102 surrounding the heater 114 along a length of the heater 114 (and the liquid container 110 surrounding the wick 102 along a length of the wick 102) may allow for aerosol to be generated evenly along the length of the heater 114 and hence along the length of the channel 124. This may allow for a consistent aerosol delivery and hence user experience. This may also allow for a more even heating along the length of the material element 126 by relatively hot aerosol being generated in the vicinity of the heater 114. The channel 124 defined by the heater 114, the receptacle 128, and the material element 126 being substantially cylindrical and concentric may allow for an even heat transfer to the material element 126. This may provide for a more consistent constituent release and hence user experience.

The channel 124 in which the material element 126 is received being defined in the heater 114 for volatilising liquid may provide for a space efficient arrangement, for example as compared to providing the material element 126 and the heater 114 in different regions of an apparatus or cartridge. The channel 124 defined by the heater 114 being cylindrical, and the wick 102 being annular and substantially surrounding the heater 114 along a length of the heater 114, and the liquid container 110 being annular and substantially surrounding the wick 102 along a length of the wick 102, may provide for a space efficient arrangement.

In use, the material element 126, or at least an outer portion or the surface of the material element 126, for example tobacco, may be heated by the heater 114 (either directly or via the aerosol produced thereby) to a temperature of between around 30° C. to 200° C. so as to improve the release of constituents therefrom as compared to ambient temperatures. For example, the heating element 114a may be resistively heated to a temperature of between around 220° C. and 270° C. The material element 126, or at least an outer portion or the surface of the material element 126, may be heated to a temperature close to (for example around between around 20° C. and 70° C. lower than) the temperature to which the heating element 114a is resistively heated. For example, the material element 126, or at least an outer portion or the surface of the material element 126, may be heated to a temperature up to around 200° C. The material element 126 may be heated only by the heater or may be additionally heated by vapour or aerosol with a temperature higher than the temperature of the material element 126 passing through the material element 126. It will be appreciated that any temperature above ambient temperature of the material and/or above the ambient temperature of the apparatus 100 as a whole may improve release of constituents from the material element. It will be appreciated that other temperatures may be used. For example, the material element 126, or at least the surface of the material, may be heated to a temperature above 200° C., such as up to around 230° C. or 240° C. or so and even as high as 290° C. or so. The amount of tobacco present may be for example in the range 50 to 300 mg or so, for example in the range 50 to 150 mg, for example 130 mg.

In the above examples, the aerosol generation was controlled via the button 118 of the battery portion 104. In other examples (not shown), the aerosol generation may be controlled by a puff detector (not shown) or any other suitable control means.

In the above examples, the channel 124 and receptacle 128 are cylindrical, the wick 102 and liquid container 110 are annular, and each are concentric. In other examples (not shown) the channel 124, receptacle 128, wick 102 and liquid container 110 may have other forms and may be arranged differently with respect to one another. For example, the channel 124 and/or the receptacle 128 and/or the wick 102 and/or the liquid container 110 may be substantially cuboidal (not shown), substantially elliptical (not shown) or a substantially hexagonal prism (not shown). In some embodiments, the channel 124 and/or the receptacle 128 may be substantially elliptical (not shown) or a substantially hexagonal prism (not shown).

In the above examples, the heating element 114a is in a coiled arrangement around the channel 124. In other examples (not shown), the heating element 114a may not be coiled, and may instead, for example, comprise one or more portions, for example individual loops of wire (not shown), for example electrically connected to one another, and/or each electrically connectable to the battery 116.

In the above examples, the heater 114 and the wick 102 are provided as separate elements. In other examples (not shown), the wick 102 and the heater 114 may be provided as an integral unit. For example, in some examples (not shown), the wick 102 and the heater 114 may be replaced by a porous ceramic heater (not shown). The porous ceramic heater (not shown) may be a porous ceramic tube type heater. The porous ceramic heater (not shown) may comprise a ceramic heating element (not shown) arranged to draw liquid from the liquid container 110, for example by capillary action. The ceramic heating element may be caused to heat up by passing a current (for example from the battery 116, and controlled by the button 118) through the ceramic heating element (not shown) causing resistive heating. For example, the ceramic heating element may be a positive thermal coefficient (PTC) ceramic element. The ceramic heater (not shown) may define the channel 124. The ceramic heater (not shown) may be substantially annular in shape, and may substantially surround the channel 124 along a length, for example the entire length, of the channel 124. The liquid container 110 may substantially surround the ceramic heater (not shown) along a length, for example the entire length, of the ceramic heater (not shown).

In the above examples, the receptacle 128 is provided separately to the cartridge 106 and is (removably) connected to the mouthpiece 108. In other examples (not shown), the receptacle 128 may be part of the cartridge 106. For example, the receptacle 128 may be (removably) connected to the cartridge 106, for example (removably) attached to the liquid container 110, for example via a lip (not shown) that holds the receptacle 128 in position in the channel 124. As another example, the receptacle 128 may be received in the channel 124, and may be so dimensioned to be held in the channel 124, for example by friction fit.

In the above examples, the material element 126 is received in the receptacle 128, and the receptacle 128 is received in the channel 124. In other examples (not shown), there may be no receptacle 128, and the material element 126 may be received directly in the channel 124. For example, the material element 126 may be self-supporting. For example, the material element 126 may be or comprise a self-supporting rod of material, for example tobacco, for example so as to be insertable into and/or removeable from the channel 124 as substantially one piece. The material element 126 may comprise material, for example tobacco, wrapped in a porous membrane. As another example, the material element 126 may be or comprise a flavour substrate material that is self-supporting. For example, the material element 126 may be or comprise a cellulose acetate rod, for example carrying a flavour releasable from the substrate so as to modify a flavour or other property of aerosol passing therethrough. The material element 126 may be attached or attachable to the mouthpiece 108. This may facilitate insertion, removal and/or replacement of the material element 126 into the channel 124. The material element 126 may be similarly proportioned to the channel 124, for example for a snug or close fit of the material element 126 into the channel 124. This may provide that the heater 114 is adjacent to the material element 126 received in the channel 124, and hence allow for improved heating of the material element 126. This may also provide for a friction fit of the material element 126 into the channel 124. The material element 126 may be substantially cylindrical. The material element 126 may be elongate and substantially circular in cross section. This may provide for even heating of the material element 126. It will be appreciated that, in other examples, the shape of the cross section of the material element 126 may not be circular, and that other shaped cross-sections may be used, for example square, elliptical or hexagonal, for example. The material element 126 may extend along the length of the channel 124 when received therein. A diameter of the material element 126 may be substantially equal, or slightly less than, a diameter of the channel 124. A diameter of the material element 126 (i.e. the diameter to the outer surface of the material element) may be in the range of from about 9 mm to 20 mm, for example in the range of from 9 mm to 15 mm or from 14 mm to 19 mm.

In the above examples, the liquid container 110, the wick 102, the heater 114 and the channel 124 were part of a cartridge 106 for connection or installation into an overall aerosol-generating apparatus 100. However, in other examples, these features may not be provided in a removable cartridge, and instead one or more of these features may be integral to an aerosol generating apparatus (not shown). In some examples therefore, there may be an aerosol-generating apparatus (not shown) comprising a liquid container for containing liquid; a wick arranged to draw liquid from the liquid container in use; and a heater arranged to volatilise liquid drawn from the liquid container via the wick in use to generate a flow of aerosol in use, wherein the heater defines a channel for receiving a material element for modifying a property of aerosol passing therethrough; and wherein the apparatus is arranged such that, in use, the flow of aerosol generated in use passes through the material element received in the channel in use, thereby to modify a said property of the aerosol.

In the above examples, the aerosol generated in use passes through the material element 126 received in the channel 124 in use thereby to modify a property, for example a flavour, of the aerosol to generate a modified aerosol for inhalation by a user. However, it will be appreciated that this need not necessarily be the case and that in other examples the aerosol generated in use need not pass through the material element 126 in order for the material element 126 to modify a property, for example flavour, of the aerosol generated in use, thereby to generate the modified aerosol for inhalation by a user. For example, the aerosol may alternatively or additionally pass over and/or around the material element 126 received in the channel 124. The material element 126 may release flavour and/or aroma or other constituents into the aerosol passing over and/or around the material element 126, thereby to generate a modified (e.g. flavoured) aerosol for inhalation by a user. In this case, for example, it will be appreciated that the mouthpiece 108 may be alternatively or additionally arranged so that the outlet 122 allows the modified aerosol (e.g. aerosol having passed over and/or around the material element and thereby picking up or entraining constituents released from the material element), to be inhaled by a user. It will also be appreciated that, in these examples, the heating by the heater 114 of the material element 126 received in the channel defined by the heater 114 may encourage release of constituents (e.g. flavour and/or aroma or other constituents that may alter a property of the aerosol) from the material element 126 into the aerosol passing over and/or around the material element 126, and hence may increase the degree of modification of the aerosol, and hence may improve user experience. It will therefore be appreciated that the material element 126 may be any material element 126 for modifying a property of aerosol (whether that aerosol passes through the material element 126 or over or around that material element 126), and that when the apparatus 100 is in use, the material element 126 received in the channel 124 modifies a property of the aerosol generated in use thereby to generate a modified aerosol for inhalation by a user.

As used herein, the terms "flavour" and "flavourant" refer to materials which, where local regulations permit, may be used to create a desired taste or aroma in a product for adult consumers. They may include extracts (e.g., licorice, hydrangea, Japanese white bark magnolia leaf, chamomile, fenugreek, clove, menthol, Japanese mint, aniseed, cinnamon, herb, wintergreen, cherry, berry, peach, apple, Drambuie, bourbon, scotch, whiskey, spearmint, peppermint, lavender, cardamom, celery, cascarilla, nutmeg, sandalwood, bergamot, geranium, honey essence, rose oil, vanilla, lemon oil, orange oil, cassia, caraway, cognac, jasmine, ylang-ylang, sage, fennel, piment, ginger, anise, coriander, coffee, or a mint oil from any species of the genus Mentha), flavour enhancers, bitterness receptor site blockers, sensorial receptor site activators or stimulators, sugars and/or sugar substitutes (e.g., sucralose, acesulfame potassium, aspartame, saccharine, cyclamates, lactose, sucrose, glucose, fructose, sorbitol, or mannitol), and other additives such as charcoal, chlorophyll, minerals, botanicals, or breath freshening agents. They may be imitation, synthetic or natural ingredients or blends thereof. They may be in any suitable form, for example, oil, liquid, solid, or powder. For example, a liquid, oil, or other such fluid flavourant may be impregnated in a porous solid material so as to impart flavour and/or other properties to that porous solid material. As such, the liquid or oil is a constituent of the solid material in which it is impregnated.

The above examples are to be understood as illustrative examples of the invention. It is to be understood that any feature described in relation to any one example may be used alone, or in combination with other features described, and may also be used in combination with one or more features of any other of the examples, or any combination of any other of the examples. Furthermore, equivalents and modifications not described above may also be employed without departing from the scope of the invention, which is defined in the accompanying claims.

The invention claimed is:

1. A component for an aerosol-generating apparatus, the component comprising:
 a liquid container for containing liquid;
 a wick arranged to draw liquid from the liquid container in use; and
 a heater arranged to directly volatilize liquid drawn from the liquid container by the wick in use to generate an aerosol in use,
 wherein the heater defines a channel for receiving a material element for modifying a property of the aerosol generated in use, and wherein the component is arranged such that, in use, the material element received in the channel in use modifies the property of the aerosol generated in use thereby to generate a modified aerosol for inhalation by a user.

2. The component according to claim 1, wherein in use the aerosol generated in use passes through the material element received in the channel in use thereby to modify the property of the aerosol to generate the modified aerosol.

3. The component according to claim 1, wherein the heater comprises a heating element substantially coiled around the channel.

4. The component according to claim 1, wherein the wick substantially surrounds the heater along a length of the heater.

5. The component according to claim 1, wherein the wick and the heater are provided by a porous ceramic heater.

6. The component according to claim 1, wherein the liquid container substantially surrounds the wick along a length of the wick.

7. The component according to claim 1, wherein the channel extends in a direction parallel to a length of the component.

8. The component according to claim 1, wherein one or both of the wick and the liquid container are annular in shape.

9. The component according to claim 1, wherein the heater is arranged to heat the material element received in the channel in use directly.

10. The component according to claim 1, wherein the component comprises a receptacle for receiving therein the material element, the receptacle being configured to be received in the channel.

11. The component according to claim 10, wherein the receptacle comprises a mesh for containing the material element and for allowing aerosol generated in use to pass therethrough.

12. The component according to claim 10, wherein the receptacle is removable from the channel.

13. The component according to claim 10, wherein the receptacle has a mouthpiece connected thereto, the mouthpiece defining an outlet for allowing the modified aerosol to be inhaled by the user.

14. The component according to claim 13, wherein the mouthpiece is removably connected to the receptacle.

15. The component according to claim 10, wherein the component comprises the material element received in the channel.

16. The component according to claim 15, wherein the material element is received in the receptacle.

17. The component according to claim 15, wherein the material element is arranged to modify one or more organoleptic properties of the aerosol generated in use.

18. The component according to claim 15, wherein the material element is or comprises tobacco.

19. The component according to claim 1, wherein the component is a cartridge for the aerosol generating apparatus.

20. An aerosol-generating apparatus comprising the component according to claim 1.

21. The aerosol generating apparatus according to claim 20, comprising:

a battery portion arranged to provide electrical power to the heater.

22. An aerosol-generating apparatus comprising:
a liquid container for containing liquid;
a wick arranged to draw liquid from the liquid container in use; and
a heater arranged to directly volatilize liquid drawn from the liquid container by the wick in use to generate an aerosol in use,
wherein the heater defines a channel for receiving a material element for modifying a property of said aerosol generated in use, and wherein the apparatus is arranged such that, in use, the material element received in the channel in use modifies the property of the aerosol generated in use thereby to generate a modified aerosol for inhalation by a user.

23. A method of generating a modified aerosol for inhalation by a user, the method comprising:
providing an aerosol-generating apparatus comprising a component that comprises: a liquid container for containing liquid; a wick arranged to draw liquid from the liquid container in use; and a heater arranged to directly volatilize liquid drawn from the liquid container by the wick in use to generate an aerosol in use, wherein the heater defines a channel for receiving a material element for modifying a property of the aerosol generated in use, and wherein the component is arranged such that, in use, the material element received in the channel in use modifies the property of the aerosol generated in use thereby to generate a modified aerosol for inhalation by a user,
directly volatizing, by the heater, liquid draw in from the liquid container by the wick, thereby to generate an aerosol; and
modifying, by a material element received in the channel defined by the heater, a property of the aerosol, thereby to generate the modified aerosol for inhalation by a user.

24. The method according to claim 23, wherein modifying the property of the aerosol comprises passing the aerosol through the material element received in the channel defined by the heater.

* * * * *

UNITED STATES PATENT AND TRADEMARK OFFICE
CERTIFICATE OF CORRECTION

PATENT NO. : 11,623,053 B2
APPLICATION NO. : 15/733181
DATED : April 11, 2023
INVENTOR(S) : Ugurhan Yilmaz and Mark Potter Page 1 of 1

It is certified that error appears in the above-identified patent and that said Letters Patent is hereby corrected as shown below:

In the Claims

In Column 14, Line 33, in Claim 23, delete "volatizing," and insert -- volatilizing --.

In Column 14, Line 33, in Claim 23, delete "draw" and insert -- drawn --.

Signed and Sealed this
Twenty-fifth Day of March, 2025

Coke Morgan Stewart
*Acting Director of the United States Patent and Trademark Office*